United States Patent
Osypka et al.

(10) Patent No.: US 8,731,670 B2
(45) Date of Patent: May 20, 2014

(54) PASSIVE ELECTRICAL CONNECTOR

(75) Inventors: Thomas P. Osypka, Palm Harbor, FL (US); Timothy L. Sass, Sr., Port Richey, FL (US); Ernest G. DeBella, Palm Harbor, FL (US); Douglas E. Sparks, Jr., New Port Richey, FL (US); Kevin L. Wade, Largo, FL (US); Kenneth R. Wilbur, New Port Richey, FL (US)

(73) Assignee: Oscor Inc., Palm Harbor, FL (US)

( * ) Notice: Subject to any disclaimer, the term of this patent is extended or adjusted under 35 U.S.C. 154(b) by 358 days.

(21) Appl. No.: 12/799,540

(22) Filed: Apr. 27, 2010

(65) Prior Publication Data
US 2011/0264162 A1    Oct. 27, 2011

(51) Int. Cl.
*A61N 1/375* (2006.01)

(52) U.S. Cl.
USPC .................................. 607/37; 439/909

(58) Field of Classification Search
USPC ................................................ 439/9, 63, 909
See application file for complete search history.

(56) References Cited

U.S. PATENT DOCUMENTS

| | | | | |
|---|---|---|---|---|
| 5,968,082 | A * | 10/1999 | Heil | 607/37 |
| 7,467,013 | B2 * | 12/2008 | Tvaska et al. | 607/37 |
| 7,587,244 | B2 * | 9/2009 | Olbertz | 607/37 |
| 2008/0208279 | A1 * | 8/2008 | Janzig et al. | 607/37 |

* cited by examiner

*Primary Examiner* — Kennedy Schaetzle
*Assistant Examiner* — Erica Lee
(74) *Attorney, Agent, or Firm* — Edwards Wildman Palmer LLP; Scott D. Wofsy; Christopher J. Capelli

(57) ABSTRACT

An electrical connector is disclosed that includes an annular housing having a central aperture for receiving a connector pin and an annular contact spring disposed concentrically within the annular housing and including a plurality of circumferentially spaced apart spring arms, each spring arm having a radially inwardly extending contact pad for resiliently contacting a connector pin inserted into the central aperture of the housing.

14 Claims, 4 Drawing Sheets

PASSIVE ELECTRICAL CONNECTOR

BACKGROUND OF THE INVENTION

1. Field of the Invention

The subject invention is directed generally to electrical connectors, and more particularly, to a passive electrical connector that is adapted and configured to facilitate low insertion and extraction forces with a mating connector pin, while maintaining consistent low resistance electrical contact.

2. Background of the Related Art

Electrical stimulation devices for cardiac stimulation are well known in the medical field. Cardiac stimulation devices are used for therapeutic and/or diagnostic purposes. These devices, which include cardiac pacemakers and implantable cardiac defibrillators, generally interface with cardiac tissue by means of implantable or otherwise attachable cardiac leads. These leads employ male connector pins to operatively connect with matching receptacles located in the therapeutic and/or diagnostic devices.

Connector pins are available in various configurations which are often of standardized types readily recognized by those practicing in the art. Common connector types well known in the art currently include: IS-1 type (International Standard ISO 5841.3:2000) low profile pacing/sensing connector pins which have a 3.2 mm diameter and are available in unipolar or bipolar configurations; LV-1 type pacing/sensing connector pins which have a 1.8 mm diameter and are available in unipolar and bipolar configurations (Guidant Corporation); and DF-1 type (International Standard ISO 11318: 2002) defibrillator connector pins which have a unipolar configuration. More recently, standardized IS-4 and DF-4 quadripolar (four pole) connector pins also have become available for use.

Quick connect/disconnect female connector system adapted to receive male connector pins, such as the aforementioned standardized connectors, are known in the art, as disclosed for example in U.S. Pat. Nos. 7,422,487 and 7,585,190 to Osypka, both of which are incorporated by reference herein in their entireties. These prior art female connectors provide a secure, non-permanent mechanical engagement with a male connector pin by creating a radially inwardly directed contact force on the pin. While this connection is secure, a substantial extraction force is needed to disengage and remove the male connector pin from the female connector.

Accordingly, there is a need in the art for a passive mechanical electrical connector that is adapted and configured to facilitate low insertion and extraction forces with a mating connector pin, while maintaining consistent low resistance electrical contact.

SUMMARY OF THE INVENTION

The subject invention is directed to a passive electrical connector for use in medical devices and the like, which includes, among other things, an annular housing having a central aperture for receiving a male connector pin, and an annular contact spring disposed concentrically within the annular housing and including a plurality of circumferentially spaced apart flexible spring arms. Preferably, each spring arm includes a radially inwardly extending contact pad that is adapted and configured to make electrical contact with a male connector pin inserted into the central aperture of the housing.

In accordance with the subject invention, the contact spring and the housing are in electrical communication, preferably through mating interference contact with one another or by way of weldments or a similar mechanical connection. Preferably, the contact spring includes five circumferentially spaced apart cantilevered spring arms. However, those skilled in the art will readily appreciate that the number of spring arms can vary depending upon the size of the male connector pin mating with the annular contact spring.

Preferably, the annular contact spring includes a radially outer connective spine from which each spring arm integrally depends. Each spring arm includes a radially inwardly extending contact pad for contacting a connector pin received in the connector. Each contact pad has a chamfered leading edge surface for reducing insertion forces exerted on the connector pin. In addition, each contact pad has a generally planar upper contact surface for contacting the connector pin received by the connector.

The subject invention is also directed to a medical device, such as a cardiac stimulation device or an adapter used in conjunction with a cardiac stimulation device and a cardiac lead. The medical device includes, among other things, one or more of the passive electrical connectors described above, which may be arranged coaxially to cooperatively receive a connector pin.

These and other aspects of the passive electrical connector of the subject invention will become more readily apparent from the following description taken in conjunction with the drawings.

BRIEF DESCRIPTION OF THE DRAWINGS

So that those having ordinary skill in the art to which the subject invention pertains will more readily understand how to make and use the passive electrical connector of the subject invention, preferred embodiments thereof will be described in detail hereinbelow with reference to the drawings, wherein.

DETAILED DESCRIPTION OF THE PREFERRED EMBODIMENTS

Figure 1:
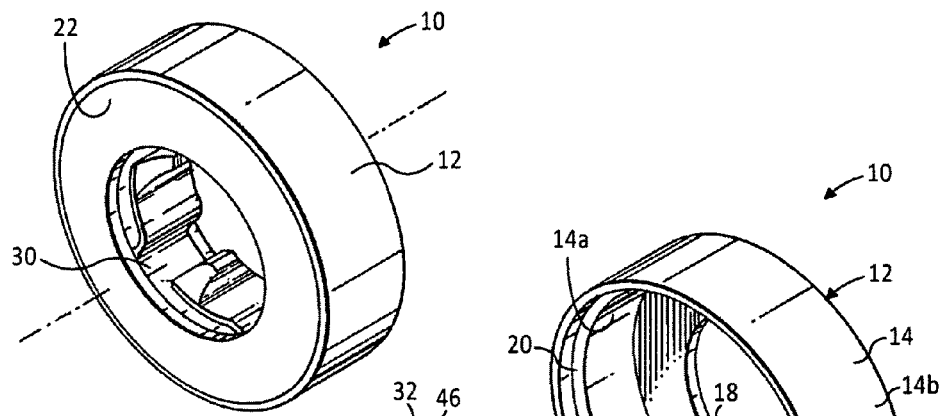
FIG. 1 is a perspective view of a passive electrical connector constructed in accordance with a preferred embodiment of the present invention.

Referring now to the drawings wherein like reference numerals identify similar structural elements of the subject invention, there is illustrated in FIG. 1, a passive electrical connector constructed in accordance with a preferred embodiment of the subject invention and designated generally by reference numeral 10.

Figure 2:
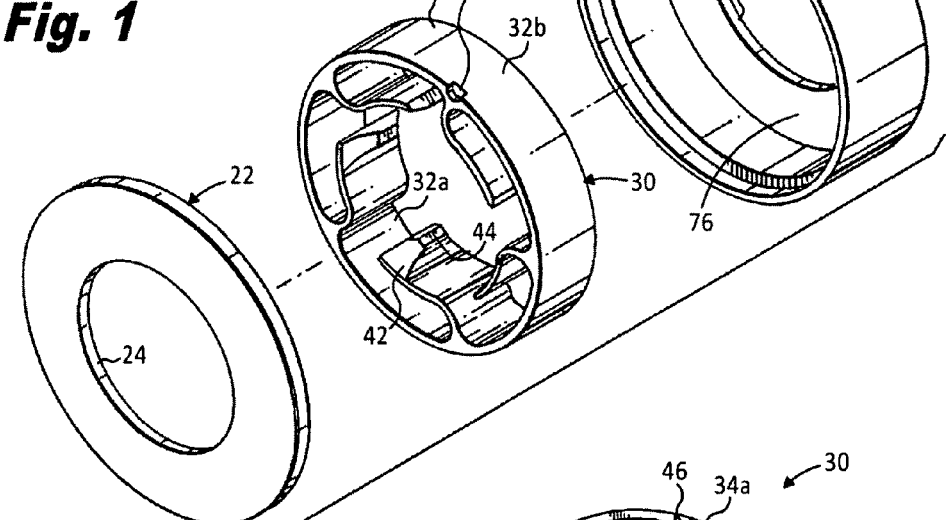
FIG. 2 is an exploded perspective view of the electrical connector shown in FIG. 1 with parts separated for ease of illustration.

Referring to FIGS. 1 and 2, electrical connector 10 includes an annular housing 12 having an annular wall 14 with inner and outer peripheral surfaces 14a, 14b and a rear face plate 16. A central aperture 18 is formed in face plate 16 and a seat or ledge 20 is formed in the inner peripheral surface 14a of the annular wall 14 opposite the rear face plate 16.

Housing 12 also includes an annular cover plate 22 which is dimensioned for accommodation in an annular seat 20. Cover plate 22 is formed with a central aperture 24 that is equal in diameter to and coaxially aligned with the central aperture 18 in face plate 16. Cover plate 22 is adapted and configured to be welded or otherwise mechanically connected to the annular housing 18, within seat 20. The housing 12 and cover plate 22 are preferably made from a material selected from the group consisting of titanium, 316L stainless steel and MP35N. However, other similar materials of construction can also be employed, depending upon the application with which the connector is used.

Connector 10 further includes an annular contact spring 30 adapted and configured to be supported within the annular housing 12 in such a manner so that the contact spring 30 and housing 12 are in electrical contact with one another. Contact spring 30 is preferably made from the same material as housing 12 and cover plate 22, namely, titanium, 316L stainless steel or MP35N. However, other similar materials of construction can also be employed.

Figure 3:
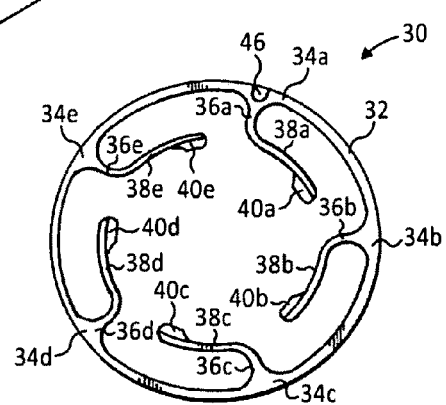
FIG. 3 is a front elevational view of the annular contact spring which forms part of the electrical connector of the subject invention.

As shown in FIG. 3, contact spring 30 includes a continuous annular spine 32 having inner and outer peripheral surfaces 32a, 32b. A plurality of cantilevered or otherwise resilient spring arms 34a-34e depend integrally from the inner peripheral wall 32a of the spine 32. The outer peripheral surface 32b of annular spine 32 is dimensioned for intimate contact with the inner peripheral surface 14a of the annular wall 14 of housing 12, thereby achieving an electrically conductive connection between the two structural components of connector 10.

The spring arms 34a-34e of contact spring 30 have respective radially inwardly extending shoulders 36a-36e and respective integrally formed, arcuately extending flexible fingers 38a-38e. The point of flexure at the junction between the shoulder and the finger of each spring arm 34a-34e enables the spring arm to make secure contact over the entire tolerance range of the mating pin inserted into the connector.

With continuing reference to FIG. 3, radially inwardly extending contact pads 40a-40e are formed at the terminal ends of fingers 38a-38e, respectively. The contact pads 40a-40e are configured to maintain consistent low resistance electrical contact with a male connector pin received within the connector 10. Each contact pad 40a-40e has a chamfered or otherwise inclined leading edge surface 42 and a generally planar upper contact surface 44, as best seen in FIG. 2. The location and size of the contact surface 44 of each contact pad 40a-40e can vary depending upon the size and type of pin with which the connector 10 is employed. The chamfered leading edge surface 42 on each contact pad 40a-40e, together with the overall resiliency of the spring arms 34a-34e themselves, promotes low insertion and extraction forces with a mating connector pin received within the connector 10.

As best seen in FIG. 2, a guide notch 46 is provided on the receiving side of the annular spine 32. This feature ensures that the contact spring 30 is properly positioned within the annular housing 12 during assembly, so that the chamfered leading edge surfaces 42 of the contact pads 40 are oriented in a direction that is appropriate to receive a connector pin.

During assembly, it is envisioned that contact spring 30 would be freely positioned within the housing 12 without being joined together. Alternatively, the two structures 12, 30 could be mechanically connected by known joining techniques.

Figure 4:
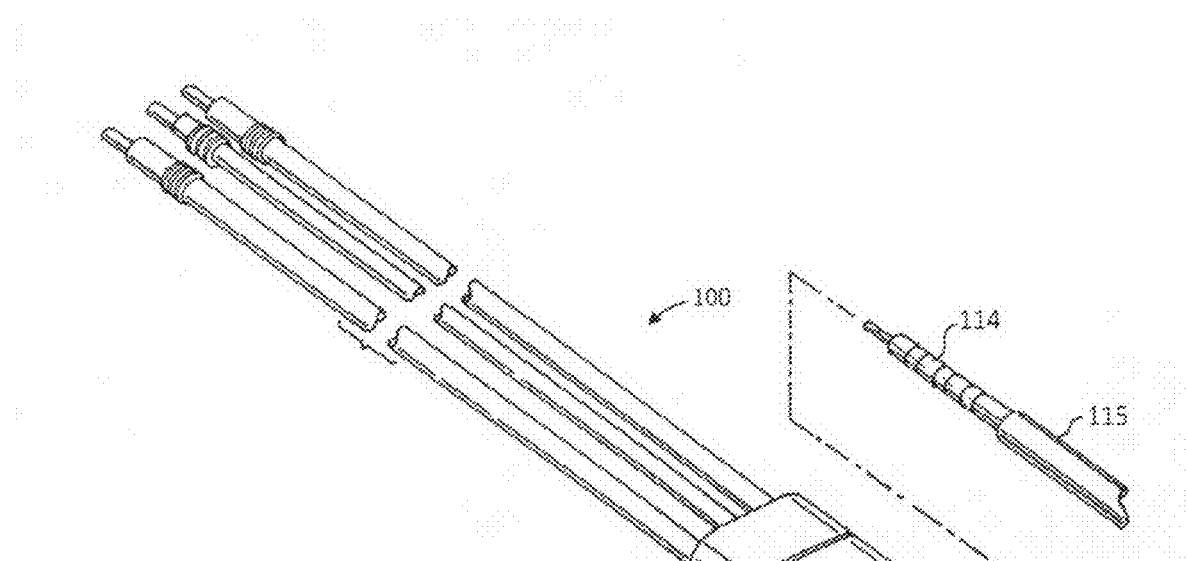
FIG. 4 is a perspective view of a medical device, in the form of a cardiac lead adapter, employing a plurality of the electrical connectors of the subject invention.

Turning to FIG. 4, there is illustrated a medical device 100 in the form of a cardiac lead adapter which includes a body 110 having a receptacle 112 for receiving an electrical connector pin 114 of a cardiac lead or the like. More particularly, as illustrated, connector pin 114 is a quadripolar (IS-4) connector pin associated with a cardiac stimulation device (not shown). Those skilled in the art will readily appreciate that the connector 10 of the subject invention can be adapted and configured to accommodate other types and sizes of connector pins, including: IS-1 type low profile pacing/sensing connector pins which have a 3.2 mm diameter and are available in unipolar or bipolar configurations; LV-1 type pacing/sensing connector pins which have a 1.8 mm diameter and are available in unipolar and bipolar configurations; and DF-1 type defibrillator connector pins which have a unipolar configuration.

Figure 5:
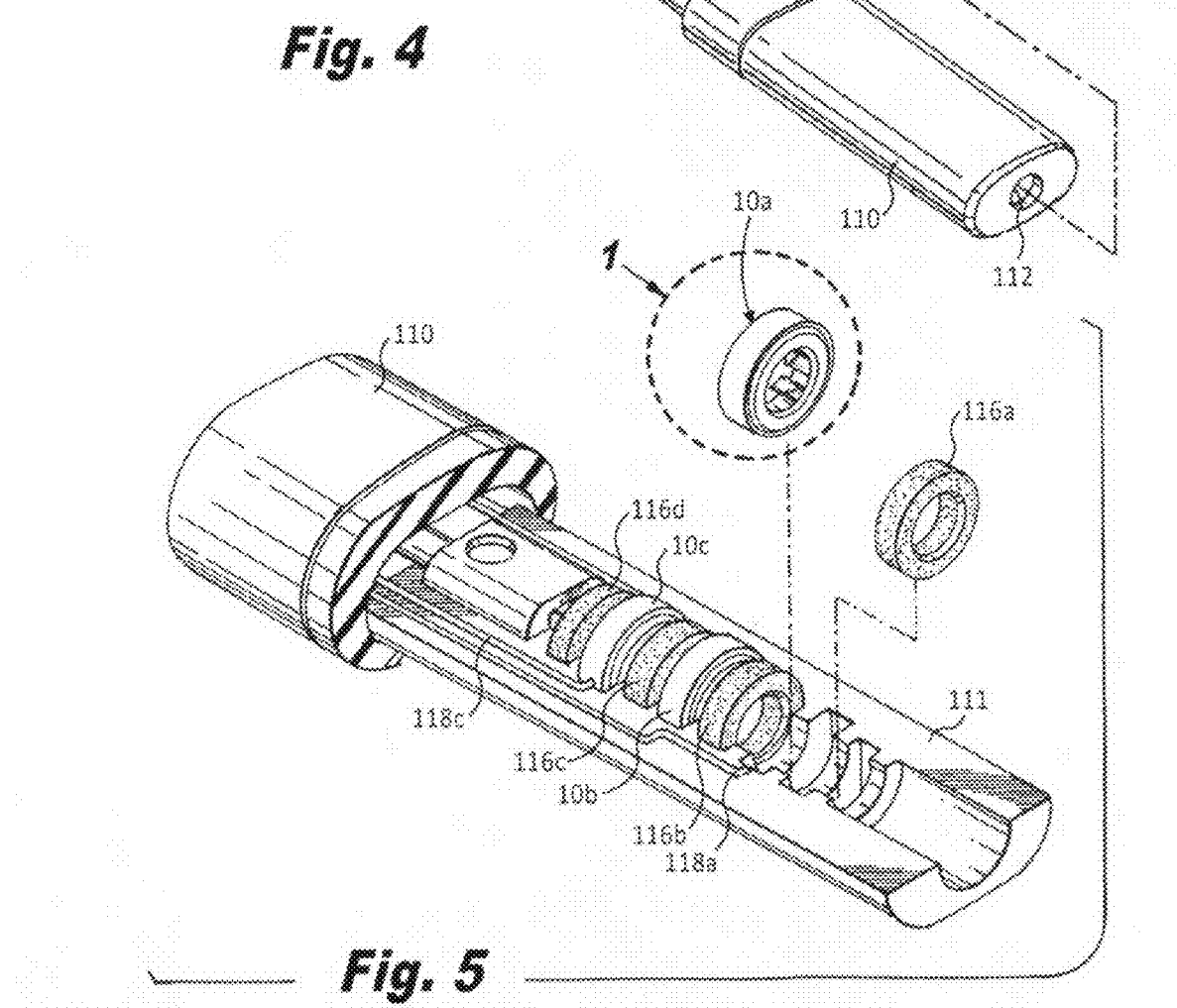
FIG. 5 is a perspective view, in partial cross-section, of the medical device of FIG. 4, showing the location of the coaxially arrangement of a plurality of electrical connectors within the body of the medical device.
Figure 6:
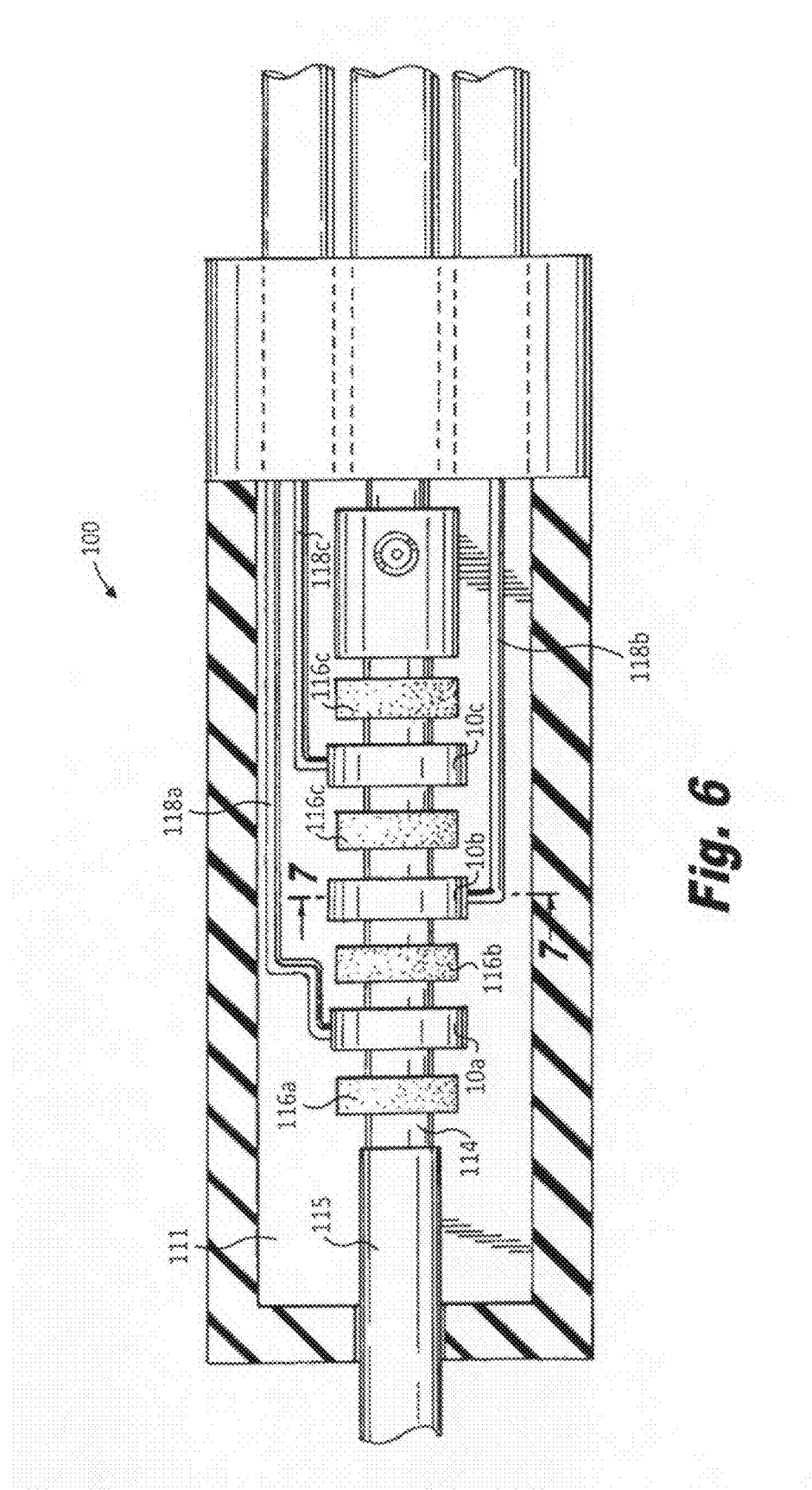
FIG. 6 is a top plan view of the medical device shown in FIG. 5.

As best seen in FIGS. 5 and 6, the interior cavity 111 of the body 110 of medical device 100 is adapted and configured to accommodate a plurality of the subject connectors 10a-10c, which are shown in coaxial alignment with the central axis of receptacle 112, and separated from one another by insulator rings 116a-116d. Each contact device 10a-10c is operatively connected to medical device 100 by way of a conductive wire 118a-118c. The conductive wires are or otherwise mechanically connected to the outer housing 12 of each connector 10a-10c, as shown for example in FIG. 8 with respect to connector 10b.

Figure 7:
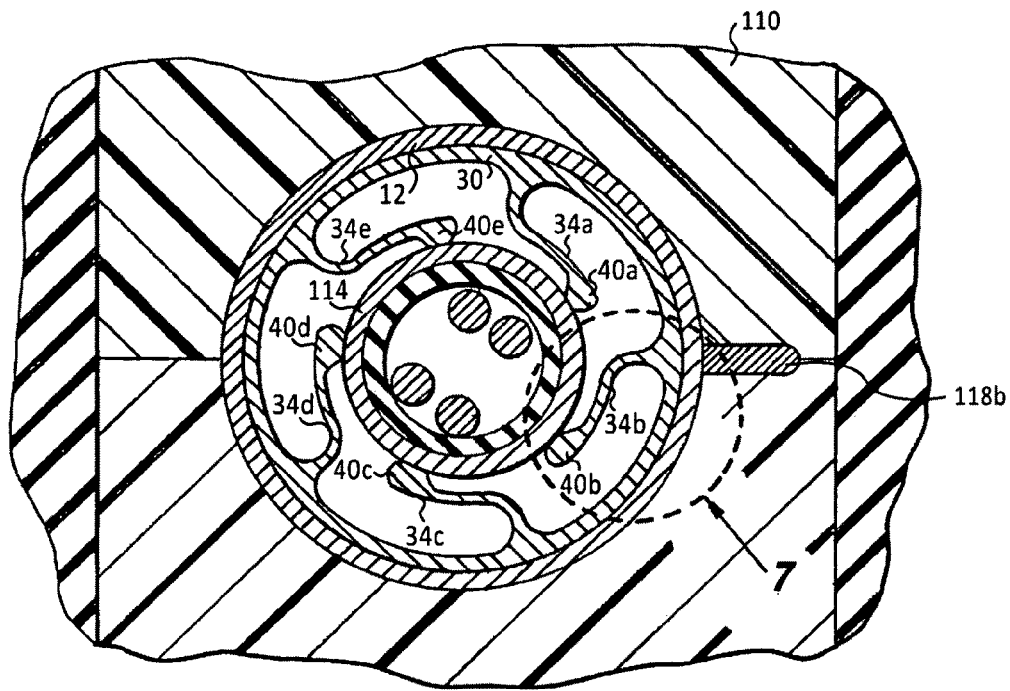
FIG. 7 is a cross-sectional view taken along line 7-7 of FIG. 6, illustrating the interaction between the female connector and a male pin received thereby.
Figure 8:
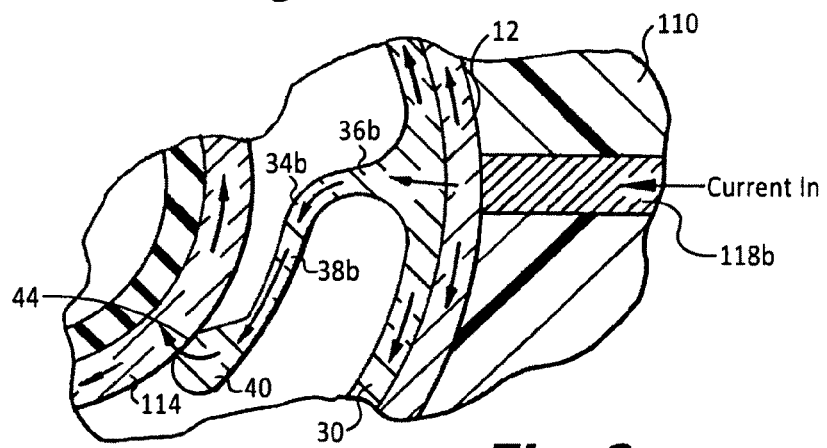
FIG. 8 is a localized view relating to FIG. 7, showing the way in which an electrical signal travels from a conductive wire associated with the medical device, through the structural components of the electrical connector, to a pin received in the connector.

During use, when a connector pin 114 of is inserted into the receptacle 112 of medical device 100, the contact pads 40a-40e of spring arms 34a-34e resiliently engage the outer periphery of the connector pin 114, as shown for example in FIG. 7 with respect to connector 10b. Those skilled in the art will readily appreciate that this is a passive mechanical engagement between the contact device 10 and the connector pin 114, since the connector pin 114 is not actively locked in a mating position within the connector 10. Moreover, the only forces exerted on the connector pin are the resilient engagement forces exerted by the spring arms 34a-34e. As shown in FIG. 8, once the connector pin 114 is engaged, an electrical signal can travel between the conductive wire 118b and connector pin 114, by way of the intimately contacting outer and inner peripheral surfaces of contact spring 30 and housing 12.

It should also be readily apparent that the electrical connector described and illustrated herein can be used in the receptacles of many other medical devices, such as pacemakers, headers, defibrillators and neuro-stimulators to cooperate with electrical connector pins of varying size and type.

Furthermore, those skilled in the art will readily appreciate that the electrical connector of the subject invention can be employed outside of the medical device field in nearly any application in which a passive mechanical/electrical connection is made by inserting a male pin into a female receptacle. For example, the electrical connectors of the subject invention can be employed in audio and video applications, wherein cables having male connector pins are inserted into components having receptacles that include one or more of the passive electrical connectors of the subject invention.

While the subject invention has been described with respect to preferred and exemplary embodiments, those skilled in the art will readily appreciate that various changes and/or modifications can be made to the invention without departing from the spirit or scope of the invention as described herein.

What is claimed is:

1. A contact device comprising:
a) an annular housing having an annular wall with inner and outer peripheral surfaces, a face plate formed integral with the annular wall and defining a central aperture for receiving a connector pin along a longitudinal pin insertion axis of the contact device, and a separate cover plate disposed opposite the face plate and defining a central aperture coaxially aligned with the central aperture of the face plate; and
b) an annular contact spring disposed concentrically within the annular housing between the face plate and the cover plate and including a plurality of circumferentially spaced apart spring arms adapted and configured to make contact with a connector pin inserted through the central aperture of the face plate and the central aperture of the cover plate, wherein the annular contact spring includes a continuous annular spine with inner and outer peripheral surfaces, wherein the outer peripheral surface of the annular spine of the annular contact spring and the inner peripheral surface of the annular wall of the annular housing are mated with one another thereby providing electrically conductive connection between the outer peripheral surface of the annular spine of the annular contact spring and the inner peripheral surface of the annular wall of the annular housing, wherein each spring arm of the annular contact spring has a respective radially inwardly extending shoulder depending from the inner peripheral surface of the annular spine and a respective integrally formed, arcuately extending flexible finger extending from said radially inwardly extending shoulder, and wherein each spring arm of the annular contact spring extends between the face plate and the cover plate so that it extends in a circumferential direction relative to the inner and outer peripheral surface of the continuous annular spine; wherein each spring arm includes a radially inwardly contact pad extending at a terminal end of the flexible finger thereof for contacting the connector pin.

2. A contact device as recited in claim 1, wherein the radially inwardly extending shoulder of each spring arm depends integrally from the inner peripheral surface of the annular spine.

3. A contact device as recited in claim 1, wherein the annular contact spring includes five circumferentially spaced apart cantilevered spring arms.

4. A contact device as recited in claim 1, wherein each contact pad has a chamfered leading edge surface.

5. A contact device as recited in claim 4, wherein each contact pad has an upper contact surface.

6. A contact device as recited in claim 1, wherein at least the annular contact spring is made from a material selected from the group consisting of titanium, 316L stainless steel and MP35N.

7. A contact device as recited in claim 1, wherein the annular contact spring and the annular housing are made from a material selected from the group consisting of titanium, 316L stainless steel and MP35N.

8. A medical device comprising:
a) a body having a receptacle for receiving a connector pin, the receptacle defining a longitudinal pin insertion axis; and
b) at least one contact device disposed within the body of the medical device, the contact device including:
  i) an annular housing having an annular wall with inner and outer peripheral surfaces, a face plate formed integral with the annular wall and defining a central aperture for receiving the connector pin along the longitudinal pin insertion axis of the contact device, and a separate cover plate disposed opposite the face plate and defining a central aperture coaxially aligned with the central aperture of the face plate; and
  ii) an annular contact spring disposed concentrically within the annular housing between the face plate and the cover plate and including a plurality of circumferentially spaced apart spring arms adapted and configured to make contact with the connector pin inserted through the central aperture of the face plate and the central aperture of the cover plate, wherein the annular contact spring includes a continuous annular spine with inner and outer peripheral surfaces, wherein the outer peripheral surface of the annular spine of the annular contact spring and the inner peripheral surface of the annular wall of the annular housing are mated with one another thereby providing electrically conductive connection between the outer peripheral surface of the annular spine of the annular contact spring and the inner peripheral surface of the annular wall of the annular housing, wherein each spring arm of the annular contact spring has a respective radially inwardly extending shoulder depending from the inner peripheral surface of the annular spine and a respective integrally formed, arcuately extending flexible finger extending from said radially inwardly extending shoulder, and wherein each spring arm of the annular contact spring extends between the face plate and the cover plate so that it extends in a circumferential direction relative to the inner and outer peripheral surface of the continuous annular spine; wherein each spring arm includes a radially inwardly contact pad extending at a terminal end of the flexible finger thereof for contacting the connector pin.

9. A medical device as recited in claim 8, wherein the contact spring includes five circumferentially spaced apart cantilevered spring arms.

10. A medical device as recited in claim 8, wherein the radially inwardly extending shoulder of each spring arm depends integrally from the inner peripheral surface of the annular spine.

11. A medical device as recited in claim 8, wherein at least the annular contact spring is made from a material selected from the group consisting of titanium, 316L stainless steel and MP35N.

12. A medical device as recited in claim 8, wherein the annular contact spring and the annular housing are made from a material selected from the group consisting of titanium, 316L stainless steel and MP35N.

13. A medical device as recited in claim 8, further comprising a plurality of contact devices arranged coaxially with respect to the pin insertion axis of the receptacle.

14. A medical device as recited in claim 13, wherein the plurality of contact devices are insulated from one another within the receptacle of the body.

* * * * *